United States Patent [19]
Sperling

[11] Patent Number: 5,506,633
[45] Date of Patent: Apr. 9, 1996

[54] DEVICE FOR ERG SPECTRAL PERIMETRY

[75] Inventor: Harry G. Sperling, Houston, Tex.

[73] Assignee: Board of Regents, University of Texas System, Austin, Tex.

[21] Appl. No.: 327,621

[22] Filed: Oct. 24, 1994

Related U.S. Application Data

[63] Continuation of Ser. No. 887,303, May 22, 1992, Pat. No. 5,382,987.

[51] Int. Cl.$^6$ ...................................................... A61B 3/14
[52] U.S. Cl. .......................... 351/206; 351/211; 351/213
[58] Field of Search .................................... 351/205, 206, 351/208, 209, 210, 211, 212, 213, 214, 224, 237, 239, 243, 246; 128/745

[56] References Cited

U.S. PATENT DOCUMENTS

| | | | |
|---|---|---|---|
| 3,737,217 | 6/1973 | Haines et al. | 351/211 |
| 4,279,478 | 7/1981 | Matsumura | 351/13 |
| 4,676,612 | 6/1987 | Wada et al. | 351/211 |
| 4,991,953 | 2/1991 | Pflibsen et al. | 351/206 |
| 5,046,835 | 9/1991 | Billeter et al. | 351/206 |
| 5,382,987 | 1/1995 | Sperling | 351/206 |

OTHER PUBLICATIONS

M. Korth, "E.R.G. Responses to Patterned Light Stimuli", *Journal of Physiology*, 337, pp. 453–456, 1983.
"Optics and information theory", *The New Encyclopedia Britannica*, vol. 25 pp. 211–213, 1989—Chicago, Il.
H. G. Sperling & S. L. Mills, "Origins and Growth of Opponent Interactions In Normal and Blue–Blind Rhesus Monkey Retina", *Die Farbe*, 34 pp. 137–143, 1987.
M. Korth & R. Rix, "The Pattern ERG In Response To Colored Stimuli", *Documenta Ophthalmologica*, 65, pp. 71–73, 1987—Netherlands.
Arne Troelstra and Charles A. Garcia, "The Electrical Response of the Human Eye to Sinusoidal Light Stimulation", *IEEE Transactions on Biomedical Engineering*, vol. BME–22, No. 5, pp. 369–378, 1975.
M. Korth & R. Rix, "Luminance–Contrast Evoked Responses And Color–Contrast Evoked Responces In The Human Electroretinogram", *Vision Res.*, vol. 28, No. 10, pp. 1277–1278, 1989—Great Britain.
S. Wu & J. Armington, "Isolation of Scotopia Human Electroretinograms Using Color Adaption And Pattern Reversal Stimuli", *Vision Res.*, vol. 29, No. 10, pp. 1277–1278, 1989—Great Britain.
S. Mills & H. Sperling, "Red/green opponency in the rhesus macaque ERG spectral sensitivity is reduced by biculline", *Visual Neuroscience*, 5 pp. 217–221, 1990—USA.
J. Simpson—Printout of Computer Search for H. Sperling of Foreign and USA Patent Databases: Files 350 and 351 of Derwent's World Patents, Files 340 and 341 of US Patent Claims, pp. 17–33, Jan. 3, 1991—Houston, TX.
L. Fredin, "ERG Spectral Perimetry System For Glaucoma Diagnosis", Grant Application—US Department of Health and Human Services, pp. 1–24, Aug. 12, 1991—Woodlands, TX.
"Announcement for granting of U.S. Patent No. 4,386,831", *Official Gazette*, pp. 142–143, Jun. 7, 1983—Washington, DC.
Biomedical Engineering, vol. BME–22, No. 5, pp. 369–378, 1975.
John B. Welrich, Theodore E. Zaleski Jr., and Steve L. Tyler, "One–Trip, Multizone Gravel–Packing Technique for Low–pressure, Shallow Wells", SPE Production Engineering, pp. 356–360, Nov. 1990.

*Primary Examiner*—William L. Sikes
*Assistant Examiner*—Hung Xuan Dang
*Attorney, Agent, or Firm*—Arnold, White & Durkee

[57] ABSTRACT

The invention features a three path Maxwellian view optical system by which a stimulus test pattern may be ophthalmoscopically placed on small portions of the central 70° of the retina of an eye. In alternative embodiments, different test patterns may be used to obtain data relating to flash ERG, pattern ERG (PERG), or flicker photometry. The location of the stimulus test target on the retina may be tracked and recorded by a spectral perimetry system. The invention further provides a spectral sensitivity measurement system in which electroretinogram (ERG) data is collected, transmitted, processed, and displayed or stored.

23 Claims, 7 Drawing Sheets

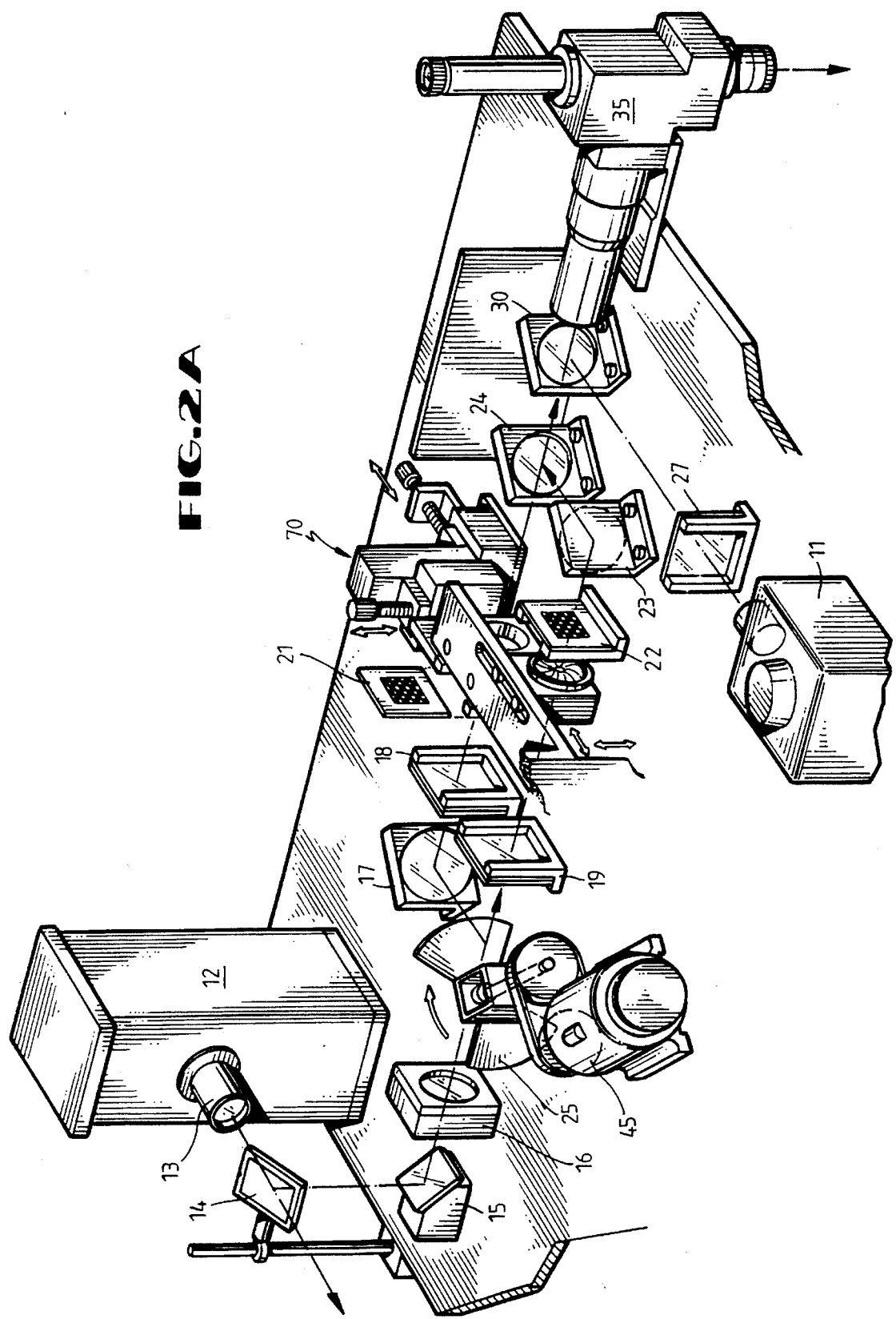

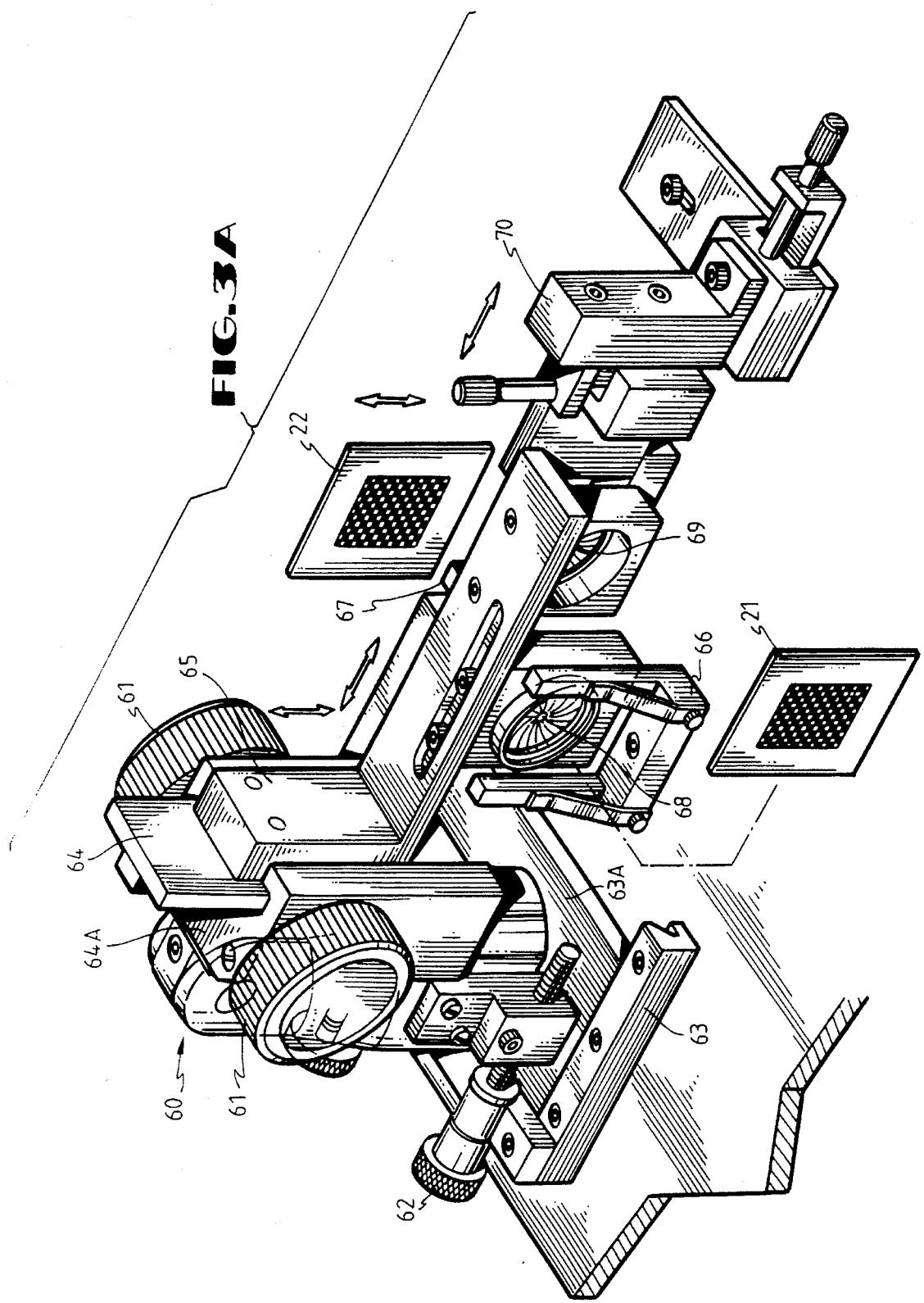

DEVICE FOR ERG SPECTRAL PERIMETRY

This application is a continuation of application Ser. No. 07/887,303, filed May 22, 1992 now U.S. Pat. No. 5,382,987.

BACKGROUND OF THE INVENTION

1. Field of the Invention

The present invention generally relates to an apparatus and method for eye examination. In particular, the invention relates to a method and apparatus for ophthalmoscopically projecting a stimulus test target onto a portion of the retina of an eye so as to create a test target. The position of the test target may be determined and recorded using a spectral perimetry system. The invention also permits spectral sensitivity measurement using collected electroretinogram (ERG) data and allows this data to be recorded and stored.

2. Description of the Prior Art

A number of methods and devices are known for examining the retina of a human eye. Often these methods and devices involve imaging devices. One such device is described in U.S. Pat. No. 4,676,612 issued to Wada et at. Wada et al. describes an apparatus comprising a target projecting system for projecting onto a retina a target image to be measured; a focalizing means, such as a TV monitor, for detecting the focus of the target to be measured and for focalizing it on the retina; an optical transfer function measuring system for detecting and measuring the contrast of the target image to be measured. The apparatus may further comprise means for comparing the measured optical transfer function with that of a normal eye and means for rotating the target image around an optical axis.

U.S. Pat. No. 4,279,478 issued to Matsumura also discloses an eye examining instrument for examination of the retina. Matsumura's apparatus uses a fixation object for maintaining the direction of the eye's line of vision, and a bright test object movable in a plane conjugate with the fundus of the eye with respect to an observation optical system. The eye fundus image is guided to an image pickup tube and displayed on a Braun tube. Recording paper and a marker cooperating with the test object are also provided for memorizing the position of the test object each time the examination is completed. Images of the marks recorded on the recording paper are superimposed on the eye fundus image, observed, and photographed.

U.S. Pat. No. 4,991,953 issued to Pflibsen et al. describes a scanning laser vitreous camera for imaging the vitreous of an eye. The apparatus features an imaging instrument wherein optics define first and second symmetrically placed windows in the iris through which a slit illumination and an observation beam synchronously scan a region of the vitreous. In a preferred embodiment, the observation and illumination paths are alternately interchanged to produce a pair of stereo images formed along identical optical paths. Alternately, a common scanning element illuminates the vitreous, which is viewed along symmetrical left and right observation imaging paths.

Physicians have recorded ERG responses to a number of different stimuli. A pattern onset-offset technique has been used which employs color-contrast patterns composed of elements discriminable only by hue but not by brightness or saturation. See 28 M. Korth et al., Luminance-Contrast Evoked Responses and Color-Contrast Evoked Responses in the Human Electroretinogram, *Vision Res.* 41 (1988).

An earlier version of Korth's work studied the transitions between pattern and luminance-related responses. See M. Korth, E.R.G. Responses to Patterned Light Stimuli, (1983). There Korth produced pattern onset-offset stimuli using a projected target beam split into two parallel paths and recombined into a single beam. While the beam is split, a shutter along one path is opened or closed to increase or decrease the light content along that path in association with pattern onset and offset resulting from the degree of vibration of the pattern.

Color flash stimulation has also been used to generate ERG data and has been reported in S. Mills & H. Sperling, Red/green Opponency in the Rhesus Macaque ERG Spectral Sensitivity is reduced by Bicuculline, *Visual Neuroscience* 217 (1990).

Other work has employed pattern reversal stimulation to evoke ERG responses using temporal alternations of a 500 nm checkerboard stimulus pattern superimposed on a uniform monochromatic field of experimentally variable wavelength. S. Wu & J. Armington, Isolation of Scotopic Human Electroretinograms Using Color Adaptation and Pattern Reversal Stimuli, *Vision Res.* 1277 (1989).

There is known in the art a hand held ophthalmoscope which projects flash ERG stimuli. This stimulator is rumored to have been modified to also incorporate pattern ERG, but not yet successfully. This device has no features for perimetry or spectral sensitivity determination.

The above described systems, while useful, do not permit a physician to examine smaller areas within specific retinal locations and to use Maxwellian view optics to stimulate the small areas at high radiance levels in order to obtain large ERG signal amplitudes for analyses. Further, these systems do not permit measurement of spectral sensitivity at different positions on and at different afferent stages of the retina.

SUMMARY OF THE INVENTION

The invention provides an apparatus and method to measure the electrical response of the retina to lights of different colors and spatial frequencies at specified and controllable retinal loci with sufficiently small yet intense stimuli to provide a fine grain map of localized changes in function. In its preferred embodiment, the invention provides for "pattern reversal" stimulation to excite ganglion cells (third order) while allowing overall luminance to remain constant.

In one application of the method and apparatus of this invention the ganglion cells of the eye, which are known to die in glaucoma related diseases, can be selectively stimulated. In the current state of diagnostic medicine, about one half of the ganglion cells are dead before their death is detected. Use of the apparatus and method of this invention permits early and accurate identification of glaucoma-related problems. In some instances, early detection can prevent blindness. Furthermore, the method and apparatus of this invention are especially suited to identify the loss of "blue response", a condition which occurs in the onset of glaucoma, before red and green losses are noted. Each of the above is a diagnostic advantage not possible with known prior art devices.

The invention includes a three-path Maxwellian view ophthalmoscopy assembly by which an image containing a flashing or pattern alternating stimulus test target may be ophthalmoscopically placed on small portions of the retina of an eye. The image is comprised of flashing discs of light or alternating test pattern projections within a neutral background field. In alternative embodiments, different test patterns may be used to obtain data relating to flash ERG, flicker photometry, i.e., ERG or psychophysical threshold determination.

Flash ERG is the massed potential as a function of time following the initiation of a flash stimulus. It has, separated in time (a) an initial negative deflection called the a-wave which comes from the rods and/or cones of the eye, (b) a large positive deflection called the b-wave initiated in the (second order) on-bipolar cells, (c) a second negative deflection called the c-wave which is of little interest, (d) a positive deflection occurring with the offset of the stimulus, probably initiated in the off-bipolars.

Flicker-photometric ERG is a technique wherein the b-wave is titrated to find the intensity of the stimulus light which when alternated with a constant (standard stimulus) light produces a minimum b-wave. This is a technique for objective light measurement. Using different wavelengths of lights alternated with a standard white light it is used to measure the spectral sensitivity of the eye.

The location of the stimulus test target on the retina may be tracked and recorded by a spectral perimetry system. This system provides a means for positioning the test target in a particular location upon the retina. It also includes a means for tracking said location which, in preferred embodiments, comprises an x-y position sensing device, such as a radial potentiometer, for tracking movement of coordinates on the diaphragm for the two alternating beams within the field of view.

The invention further provides a spectral sensitivity measurement system in which electroretinogram (ERG) data is collected, transmitted, processed, and displayed or stored. The system also provides a wide-field ophthalmoscopic view of the retina, upon which the target may be placed to test selected areas of the retina.

In an alternate preferred embodiment of this invention one or more CRT (cathode ray tube) devices are used to replace the ophthalmoscopic assembly previously described. Such a specialty adapted CRT device could display the necessary pattern for transmission to the retinal surface and could at the same time provide the necessary illumination to provide viewing by the attending physician. The CRT device could be used as a single device as the sensitivity of the retinal service of each eye was measured separately or could be used in combination to measure both eyes simultaneously.

BRIEF DESCRIPTION OF THE DRAWINGS

Further details are explained below with the help of the examples illustrated in the attached drawings in which:

FIG. 2A is a perspective view of one embodiment of the spectral perimetry stimulation apparatus according to the present invention.

FIG. 3A is a schematic representation of the stimulus positioning assembly according to the present invention.

DETAILED DESCRIPTION OF THE PREFERRED EMBODIMENTS

Figure 1A:
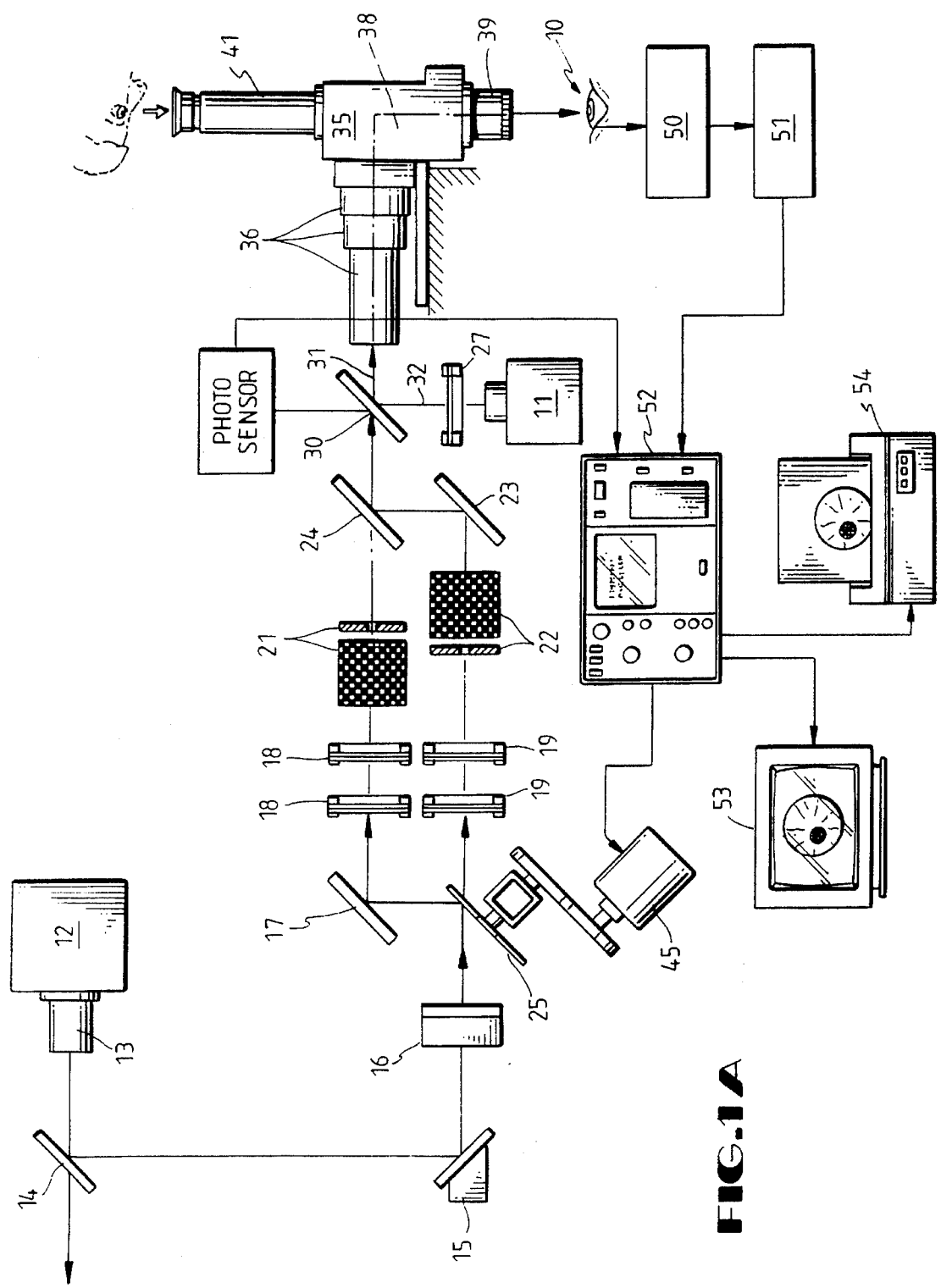
FIG. 1A depicts a schematic representation of an ophthalmoscopy assembly according to the present invention showing the reticles in both the normal position perpendicular to the light path and in planar representation.
Figure 1B:
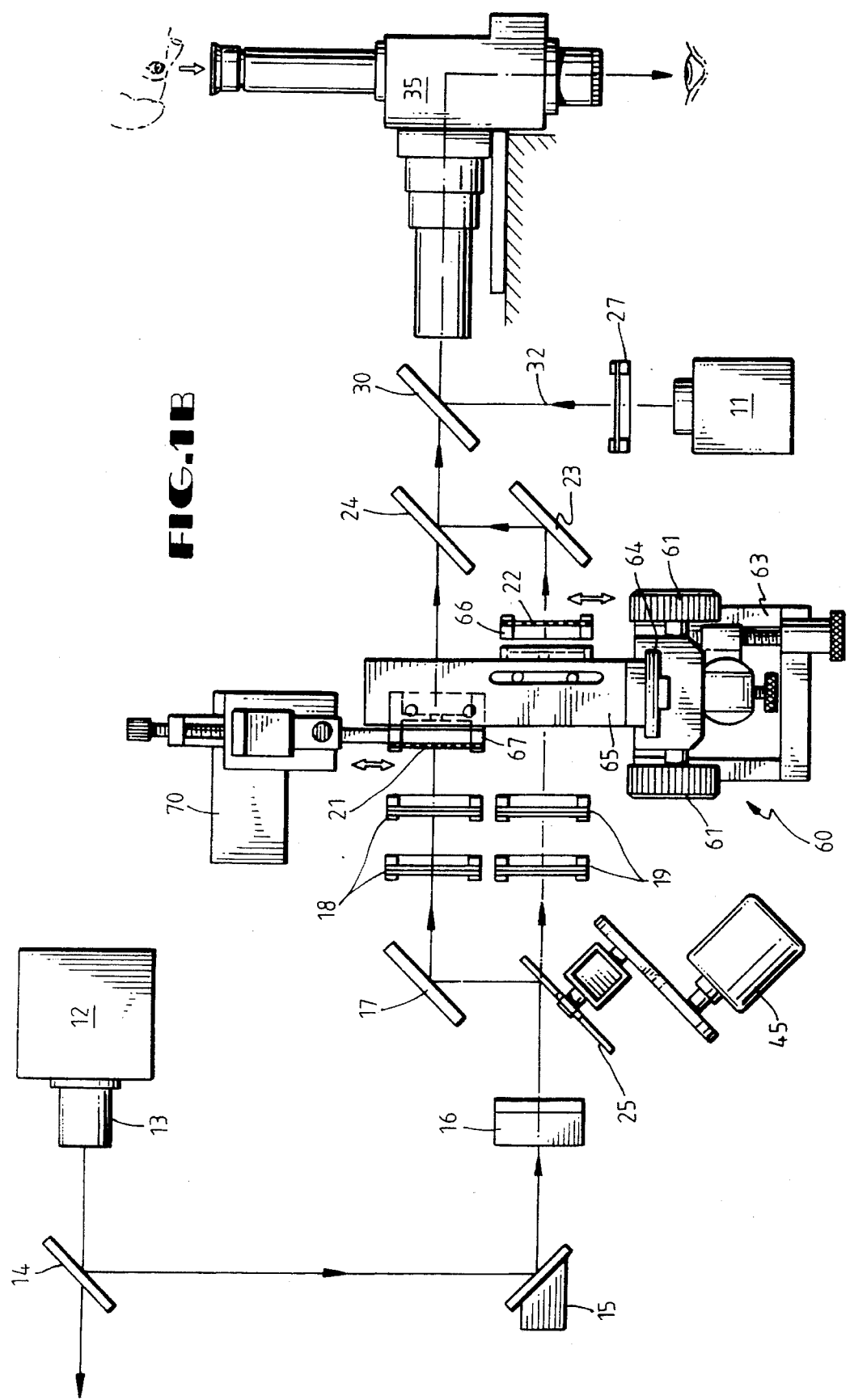
FIG. 1B is a schematic representation similar to that shown in FIG. 1A but with the stimulus positioning assembly shown in greater detail.

A preferred embodiment of the present invention is depicted in FIGS. 1A and 1B. In accordance with the present invention, there is provided a three-path Maxwellian view ophthalmoscopy assembly to project an image containing a stimulus test target onto a portion of the retina of an eye 10. For purposes of this invention the phase "ophthalmoscopy assembly" will be used interchangeably with the phrases "optical stimulus apparatus for ERG measurement" and "optical projection assembly." Preferably, a single beam creates a background light path while a second beam, or target beam, is initially split into two parallel light beam paths.

As shown in FIGS. 1A and 1B, the ophthalmoscopy assembly portrayed features a first light source 11 and second light source 12. The first light source 11 produces a background light, and, in a particularly preferred embodiment, comprises a tungsten halogen lamp which provides a 70° intense neutral background. Second light source 12 may, in one embodiment, comprise a xenon arc lamp. The ophthalmoscopic subsystem may also include condenser lens 13, cold mirrors 14 and 15, collimator 16, and back mirror 17. Condenser lens 13 is a type of lens known in the art for collecting energy from a light source. Cold mirror 14 is a heat transmitting mirror of a type known in the art which transmits infrared radiation while reflecting visible light. It is highly preferred that cold mirror 14 be placed at a 45° angle to its light source thereby permitting the infrared radiation to be transmitted undeviated while reflecting the visible light at a 90° angle from said light source. Collimators, such as collimator 16, are devices known in the art for producing relatively parallel beams of light. Preferred collimators are those which use color correction to bring as much of the spectrum as possible to the same focus.

Beam splitters 24, 30 and 38 may comprise a number of devices which reflect a portion of a light beam while transmitting another portion of the light beam. Such devices are well known in the art and include plate, pellicle cube-type beam splitters, and bifurcated fiber optic bundles which represent exemplary types of beam splitters. Back mirror 17 comprises a plane, front-surface mirror to reflect a beam path.

The ophthalmoscopic subsystem may further include neutral density wedges 20, neutral density filters, and interference filters. It is highly preferred that these components be placed, individually or in combination, along the split beam paths between the beam splitter and the reticles. Holders 18 and 19 are shown schematically in FIG. 1 and are adapted to hold such neutral density filters and interference filters. In a preferred embodiment of this invention the holders 18 and 19 are supplemented by neutral density wedges 20. In such a preferred embodiment various combinations of neutral density filters and interference filters can be used in combination with the neutral density wedges. Interference wedges could be used to replace the interference filters. The wedges, interference and neutral, are continuous and can be moved via stepping motors controlled by a computer.

Neutral density wedges may comprise a number of continuously variable light attenuators which will control the intensity of a light beam by attenuating all wavelengths of the beam by relatively the same amount so that the color of said beam is not changed. An example of a commercially available neutral density wedge which has been found suitable for this application is the 28650 Circular Variable Neutral Density Filter Wheel available from Oriel Corporation of Stratford, Conn. (from Oriel Corporation catalog *Optics & Filters*, Vol III (1990)). Neutral density filters are single value light attenuators, also known in the art, which reduce the intensity of a light beam by a fixed amount without changing the beam's color. Interference filters comprise filters, such as are known in the art, which transmit a selected waveband of the spectrum and reflect other parts of the spectrum thereby producing relatively pure (narrow waveband) colors of relatively high intensity. An example of commercially available interference filters suitable for this application include the 53700 Oriel Filter Wheel with interference filters to provide transmission from 400 nm to 700 nm available from Oriel Corporation. Individual interference filters, Nos. 53800-54565, are also suitable and available from the same company.

Reticles 21 and 22 are associated with back mirror 17 and butterfly mirror 25, respectively. Reticles 21 and 22 each contain stimulus test patterns printed, etched or otherwise affixed thereon. In a highly preferred configuration for measuring pattern ERG, the patterns comprise checkerboards with alternating opaque and clear squares. In this configuration, checkerboards in reticles 21 and 22 closely mirror each other with regard to pattern size and placement within the reticle; however, a light check in reticle 21's checkerboard would correspond to a dark check in reticle 22. Tests to date have shown an optimum checkerboard pattern to have one checkerboard in each reticle, each checkerboard comprising from one to sixteen check pairs (one opaque check and an adjacent clear check) per degree of retinal angle. It is essential that reticles be used in matched pairs and that the patterns be of the exact same size. For purposes of illustration reticles 21 and 22 are shown in FIG. 1A in both their normal position perpendicular to the light path and in a schematic planar position to illustrate the checkerboard pattern.

Referring specifically to FIG. 1B reticles 21 and 22 are located in adjacent parallel beam paths. At least one of these reticles is moveable along its beam path with respect to the other reticle to permit the phase of one with respect to the other to be adjusted. With the two reticles in one position with respect to each other, the patterns will be in phase with each other; with the reticles in another position, the patterns will be 180° out of phase with each other. In a particularly preferred embodiment (see FIG. 1B and FIG. 3A), the apparatus may be provided with a reticle positioning assembly 70 to mechanically adjust the position of the patterns with respect to each other.

The stimulus positioning assembly 60 includes a base 63 in which a platform 63A is movably mounted. Member 63A permits movement of the stimulus positioning assembly in one dimension. Movement of plate 63A is effected by adjustment knob 62. Moveable plate 64 is movably mounted in vertical base 64A. Movement of plate 64 relative to base 64A provides movement of the stimulus positioning assembly in a second direction. Adjustment arm 65 is mounted to moveable plate 64 and includes mechanical means for attaching variable iris diaphragm holders 68 and 69. Variable iris diaphragm holders 68 and 69 can be adjusted but apertures in the diaphragms must always be the same size. In operation the stimulus positioning assembly of this invention is adjusted by adjustment knobs 61 and 62 to provide the precise positioning of the variable iris diaphragm holders 68 and 69. It is essential that the reticles 21 and 22 be positioned in holders 66 and 67.

Assembly 70 is used to move reticle holder 67 with respect to reticle holder 66 in order to set the phase of one checkerboard with respect to the other. In the out of phase position, a light check in a pattern projected from one reticle will correspond to a dark check in the pattern projected from the other reticle. If the patterns are viewed in succession, they will appear to be a single checkerboard (the test target) whose black/white pattern reverses itself. This "pattern reversal" stimulation excites ganglion cells (third order) while allowing overall luminance to remain constant.

In an alternative configuration for measuring pattern ERG (PERG), the reticle patterns recited above may comprise gratings (i.e., alternating light and dark lines) instead of checkerboards. For different stimuli, the patterns can be circular to provide for test targets of homogeneous circular flashing spectral lights, alternating spectral and white flashing lights, or a checker board consisting of alternating spectral (e.g., color-white or color-color such as blue-yellow and red-green) checks of constant mean luminance. Those skilled in the art will recognize that other patterns may be used as well. The ability to substitute other patterns permits the apparatus to be used to obtain data for flash ERG and flicker photometry as well.

The ophthalmoscopy assembly further includes a beam path alternator which alternately permits each target beam path to be further transmitted along a course 31 toward an eye while blocking transmission of the other target beam path. The beam path alternator further serves to portray the parallel stimulus test patterns as a single test target whose image is maintained by alternating beam paths from the second light source.

In the embodiment shown by FIGS. 1A, 1B, 2A and 3A, this beam path alternator comprises a butterfly mirror assembly 25. Butterfly mirror assembly 25 is an apparatus known in the art, the reflective surface of which provides alternating 90° mirrored and cut out portions. When placed in the path of the target beam at approximately 45° from the direction of approach of the beam paths and angularly rotated, butterfly mirror assembly 25 alternates beam transmission as described above. The butterfly mirror assembly 25 also includes a commutator for signalling the beginning of each cycle to the averaging computer.

Butterfly mirror 25 is pivotally mounted and, in a preferred embodiment, is angularly rotated by motor 45. Motor 45 may be a variable speed or single speed synchronous motor. It is highly preferred that said motor be capable of rotating said butterfly mirror at a rate which is near optimal for generation of significant ERG responses. Literature current as of the time of this patent application places such a rate as near 8 Hz.

In alternative embodiments, the beam path alternator may comprise a shutter assembly. In these embodiments, the beam paths are alternately blocked by one or more shutters so that transmission of one beam path along a single path towards an eye is permitted while transmission of the other beam path is not.

A condenser lens may be associated with first light source 11. Filter holder 27 is also shown in conjunction with light source 11. Likewise a cold mirror may also be interposed between first light source 11 and beam splitter 30. A cold mirror removes infrared radiation from the first light source's beam as described above.

In some embodiments, the ophthalmoscopy assembly may also include a collector which combines beams from the first and second light sources into a single image. The collector preferably comprises a beam splitter employed to join said beams and transmit them along a single course 31 toward the eye.

The image transmitted from the collector passes through projection lens 36 which permits the test target to be focused as necessary to create a clear image when focused upon the retina, then enters eyepiece assembly 35. Experimentation to date has shown that a zoom projection lens of about 70 to 150 mm of focal length with photographic quality color correction serves adequately for this purpose.

The ophthalmoscopic system may include a telescope 41 to aid in ophthalmoscopically placing said image onto a localized portion of the retina of an eye. An exemplary eyepiece, as more clearly seen in FIG. 1A, is preferably an articulable assembly pivotally and rotationally mounted to its base.

Figure 5:
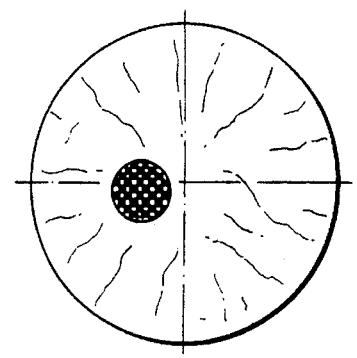
FIG. 5 is a schematic representation of the retina of the eye showing the image from the reticle focused on a specific spot.

In operation, the above described arrangement uses the first and second light sources to produce an image comprising an illuminated neutral background containing a stimulus test target. As shown in FIG. 5 the image may be ophthalmoscopically placed on the retina of an eye. First light source 11 produces the neutral background. When light source 11 is energized light enters the beam splitter/collector 30. Meanwhile, second light source 12 may be energized so that light from this light source enters condenser 13, reflects off cold mirrors 14 and 15, and is collimated by collimator 16. At this point, light from second light source 12 is split upon encountering butterfly mirror 25, such that the light beam is reflected from butterfly mirror 25 to back mirror 17 and alternately passes through the butterfly mirror. The parallel beam paths pass through reticles 21 and 22 respectively, each retical containing a stimulus test pattern. The parallel beam paths will also preferably pass through neutral density wedges 20, neutral density filters, and interference filters. The beam path which has passed through retical 21 encounters beam splitter 24, where it passes through to beam splitter 30. The beam path which has passed through reticle 22 encounters mirror 23 and is reflected to beam splitter 24 where it joins the beam from reticle 21. After passing through beam splitter 30 the beams follow beam course 31.

The light beam from beam splitter 24 is directed to beam splitter 30 where it is further combined with background light 32. The combined beams then follow path 31 into the eyepiece assembly 35. Eyepiece assembly 35 includes a projection lens 36, a cube beam splitter 38, a short focal length eyepiece 39, and telescope 41. Cube beam splitter 38 is a coated beam splitter cube that will not permit light reflected off the cornea to reach the practitioner's eyes. Light from course 31 and first light source path 32 is transmitted further into variable focus projection lens 36. Projection lens 36 is used to focus the image on the target. It is essential that during use of the apparatus of this invention that the subject patient's eye remain stationary, movement of the eye will cause corresponding discrepancies in the data collected.

Projection lens 36, which is preferably a zoom projection lens, is used to sharply focus whatever is in the image plane. Reticles 21 and 22 and the variable iris diaphragms 68 and 69 define what is in the image plane. A stationary central fixation point for use when targets are moved to different planes on the retina is also in the image plane.

The invention also features a perimetry assembly by which the location of a stimulus test target may be set anywhere in the field of lens 39 projected upon the retina and may be sensed from the stimulus positioning assembly 60 and recorded. Preferably, the perimetry system also provides means for adjusting the diameter of the projected test target. In a preferable embodiment, the stimulus positioning assembly includes a pair of diaphragms 68 and 69. The diaphragms may be adjusted by being radially opened or closed, much as the iris diaphragm of a camera, thereby changing the diameter of the projected test target. In one embodiment, shown in FIG. 3A, coordinate diaphragms are placed slightly forward of and behind the two reticles along each beam path. In this embodiment, both diaphragms must be adjusted to cause the test patterns to appear to be virtually the same size when viewed as alternating images in an alternating or flashing test target.

As may be seen in FIGS. 1B and 3A, variable iris diaphragms 68 and 69 are movable in concert with each other by means of stimulus positioning assembly 60 so that the projected test target may be moved to various places on the retina within the ophthalmoscopically visible field.

At least one commutator is functionally associated with the butterfly mirror 25 to initiate the collection of an ERG waveform in the averaging computer for each alternating cycle of the stimulus. At least two radial potentiometers are functionally associated with the stimulus positioning assembly 60 to track and record the stimulus on the retina. The voltage signal created by the radial potentiometers is transmitted to computer 52, display device 53, and printer 54. In alternate embodiments, a polar coordinate plot or a printout of the target position or both may be used.

The apparatus of the present invention further comprises a measurement assembly which is functionally integrated with the spectral perimetry assembly described above. FIG. 1A provides an exemplary arrangement of systems comprising the present invention. The measurement assembly collects, transmits and interprets electroretinogram or other data from the eye which is generated from pattern reversal stimulation of the retina by the projected test target. This assembly comprises a means for collecting ERG data from the eye, transmission means for said data, and means for displaying or storing said information. The measurement assembly may further comprise filters, a differential amplifier, means for determining a time-based average waveform, and means for determining spectral sensitivity.

Figure 3B:
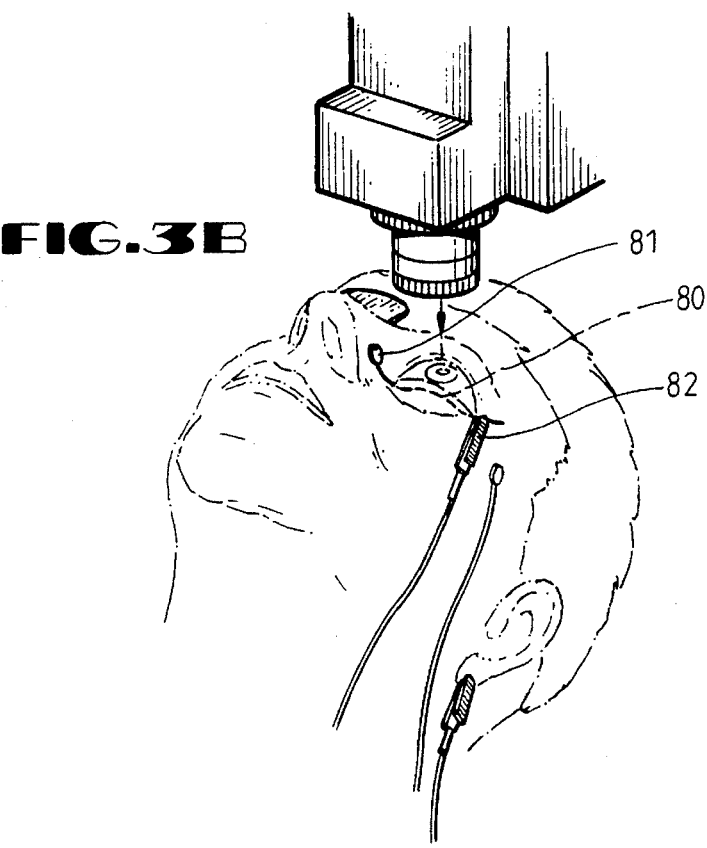
FIG. 3B is a perspective view of the electrode assembly for detecting the electrical response of the retina.

One method for collecting ERG data from the eye includes a contact lens having an embedded electrode disposed on the concave surface of the lens, said electrode including a non-polarizable conductive metallic coating. One such device is described in U.S. Pat. No. 4,109,648 issued to Pierre-Alain Grounauer of Switzerland. Sensings from electrode will travel via transmission means, which preferably comprises a conductive wire. An alternate but nevertheless preferred embodiment is shown in FIG. 3B and includes the use of a thin conductive thread 80 placed under the lower eyelid of a patient. The thread 80 is held in position by a small drop of petroleum jelly 81 on the side of the nose and an alligator clip 82 detachably mounted on the surface of the skin of the upper cheek of the patient. Other less primitive means for maintaining the position of the sensing electrode are well within the scope of this invention.

More refined embodiments of the invention include a 60 cycle filter 50 which removes ambient 60 cycle fields from the ERG signal. Additionally, a preamplifier 51 amplifies the ERG signal.

The measurement system further includes an averaging signal which permits computation of a time-based average ERG component waveform for use in the spectral sensitivity evaluation. Averaging signal may be readily generated using a voltage commutator, operably attached to the beam path alternator 25 which detects and produces a voltage signal at each beam path alternation. A spectral sensitivity evaluation device 52 (such as a specialized computer with appropriate software) which uses said waveform component amplitudes as criteria for determining spectral sensitivity. Averaging device and spectral sensitivity evaluation device 52 may comprise separate components or be combined in an apparatus, such as a personal computer, which is capable of performing both functions. In the latter instance, an analog to digital converter may be required to permit entry of the signal to be processed by the computer.

Additionally, the measurement assembly of the present invention includes a display device 53 and/or storage means for data collected from the eye and information interpreted from that data during the measurement process. In one particularly preferred embodiment, display means 53 comprises an oscilloscope. The storage means may comprise such means as on-paper recordation of numerical data points or graphs or computer storage of such data. In other preferred embodiments a printer 54 can be functionally attached to computer 52.

Figure 4:
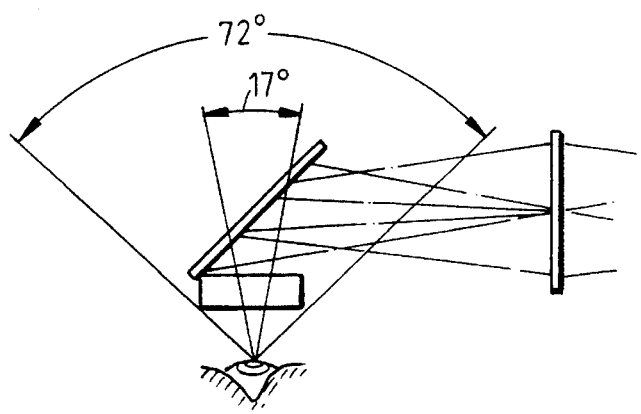
FIG. 4 is a side view of the angular field of view of the apparatus of this invention in relationship to the human eye.

In an alternate embodiment of this invention parallel laser beams are used to impinge on the retina to create a grating effect. Separation of the parallel beams, by a prism or other means, controls the spatial characteristics of the grating. The laser beams are pulsed resulting in a time modulated image, which will stimulate the ERG in repeated cycles. These would be summed in the computer as described above to provide a time-based average ERG waveform FIG. 4 illustrates angular field of view of the eyepiece lens 39 (72°) which may be filled with the checkerboard, or the checkerboard may be vignetted to any desired stimulus diameter by adjusting iris diaphragms 68 and 69 (17° shown in examples).

A spectral perimetry stimulation apparatus of the type described above has recently been used to collect and interpret spectral sensitivity data from the retinas of humans and monkeys. The results indicate that the invention may have significant application toward the early detection of inner retina degenerative diseases such as glaucoma, diabetic retinopathy, and optic atrophy.

Figure 6:
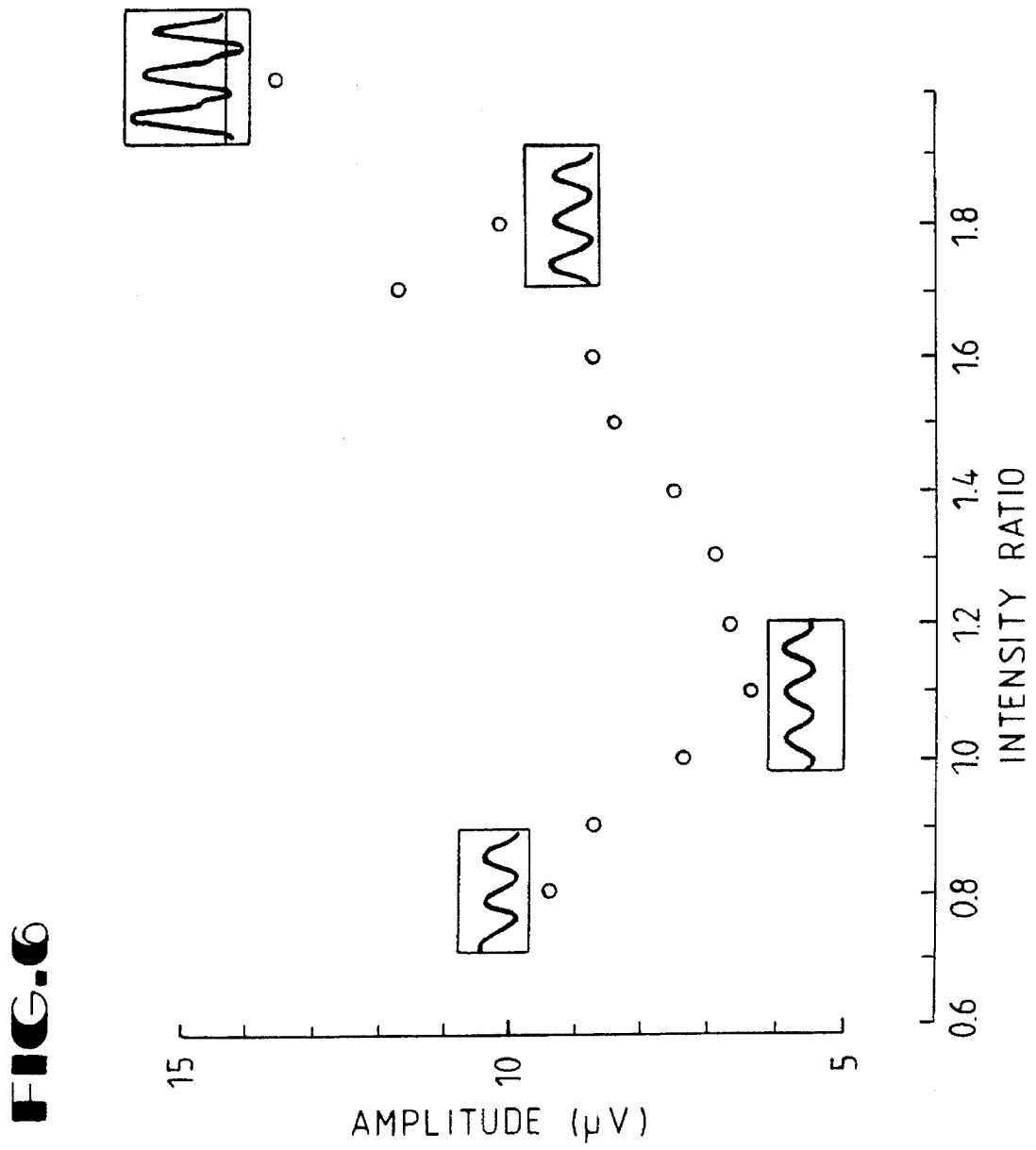
FIG. 6 is a graphic representation of ERG amplitude plotted as a function of intensity ratio and demonstrates the way in which spectral sensitivity data is obtained from ERG data.

FIG. 6 illustrates the way in which we obtain spectral sensitivity from ERG data. Every other check in the checkerboard pattern alternates between black and white on a 50/50 light dark cycle. The adjacent checks go between black and spectral on the same cycle but such that the black periods alternate. The white is fixed at a constant luminance of 12000 Trolands and is used as a standard. The spectral is varied from dimmer than the white to brighter than the white. In FIG. 6 as the ratio of spectral to white luminance varies, the ERG amplitude goes through a minimum. The light energy that produces the minimum is used to calculate the spectral sensitivity for that wavelength. In the spectral sensitivity plots the reciprocal of that energy in quanta is plotted as a function of the wavelength of the light on an equal wave number scale.

Figure 7:
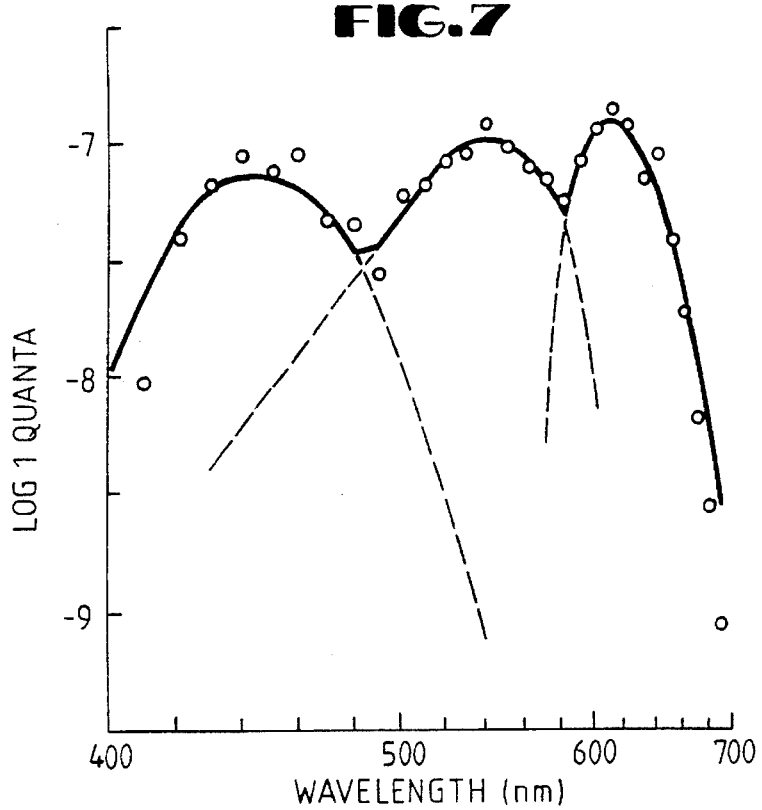
FIG. 7 is a graphic representation of the characteristic spectral sensitivity of a normal human eye.

FIG. 7 shows the characteristic spectral sensitivity of a normal human eye obtained by finding the minimum light energy that is subjectively detectable over a constant white background set near the same intensity as the white checks are set at in the ERG measurements. It characteristically shows three sensitivity peaks associated with red, green and blue response.

Figure 8:
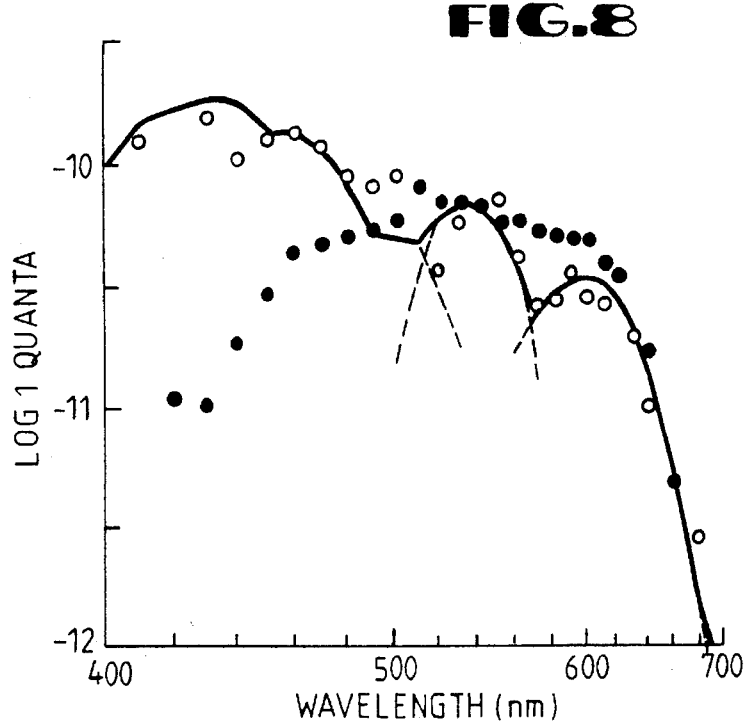
FIG. 8 is a graphic representation of the pattern ERG (PERG) data obtained over the central retina with the spectral sensitivity apparatus of this invention.

FIG. 8 shows the pattern ERG (PERG) data obtained over the (17°) central retina with the spectral ERG perimetry device. The same three peaks are obtained as in the behavioral study of FIG. 7. The filled circles were obtained with the checkerboard removed, as a control, so that large homogenous circular fields of spectral and white light of the same extent as used in the PERG experiment were alternated at the same rate and spectral sensitivity was measured in the same way. This (filled circle) data show the characteristic spectral sensitivity of bipolar cell level neural processing. The PERG data reveal a higher order of neural processing which must occur at the ganglion cells. It shows much higher blue sensitivity and a notch at 580 nm in the yellow, characteristic of red-green opponency. With the loss of ganglion cells in early open-angle glaucoma, the higher level function (open circles) should first show a reduction over the peak in the blue, then complete loss of the peak in the blue, then progressively a filling of the 580 nm notch.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and spirit of the invention. It is intended in the following claims to cover all such equivalent modifications and variations which fall within the spirit and scope of the invention.

What is claimed is:

1. A spectral perimetry stimulation apparatus adaptable for application of pattern reversal stimulation comprising:

(a) an ophthalmoscopy assembly including a three path Maxwellian view optical system, wherein said ophthalmoscopy assembly provides a first light source to create a neutral background light upon which a stimulus test pattern can be placed at a desired retinal position, said neutral background light from said first light source being configured to pass through a condenser lens, said neutral background light being focused by an eyepiece into the pupil of the eye, said ophthalmoscopy assembly being functionally effective to project a stimulus test pattern onto a localized portion of the retina of an eye under ophthalmoscopic control;

(b) a spectral perimetry assembly functionally integrated with said ophthalmoscopy assembly, said spectral perimetry system providing continuous information regarding the position of a stimulus test pattern on said retina of said eye, and (c) a measurement assembly functionally integrated with said spectral perimetry assembly, said measurement assembly providing information that permits the identification of localized changes in spectral sensitivity of said eye.

2. The apparatus of claim 1 wherein the ophthalmoscopy assembly further includes a second light source, said second light source producing a light beam which is alternately reflected and transmitted to the eye by a beam path alternator, said second light source producing a stimulus test target; said ophthalmoscopy apparatus further comprising means for splitting said light beam from said second light source into parallel beam paths, each beam path made to pass through a receptacle containing a stimulus pattern so that the beam produces a flashing or alternating stimulus test target on the retina of an eye.

3. The apparatus of claim 2 wherein light from the second light source further passes through one or more condenser lenses.

4. The apparatus of claim 2 wherein the beam path alternator comprises a butterfly mirror which is pivotally moved by means of a motor.

5. The apparatus of claim 2 wherein the beam path alternator comprises a shutter assembly.

6. The apparatus of claim 2 wherein the ophthalmoscopy assembly further comprises an eyepiece assembly, said eyepiece assembly comprising a projection lens, a beam splitter and a short focal length eyepiece.

7. The apparatus of claim 2 wherein the reticles are movable with respect to each other along the parallel beam paths so that the patterns are in spatial phase with each other with the reticles in one location and 180° out of spatial phase with each other with the reticles in the other location.

8. The apparatus of claim 2 wherein the ophthalmoscopy assembly further comprises one or more neutral density filters through which, at least one parallel beam path is configured to pass.

9. The apparatus of claim 2 wherein the ophthalmoscopy assembly further comprises one or more spectral interference filters through which at least one parallel beam path is configured to pass.

10. The system of claim 2 wherein the ophthalmoscopy assembly further comprises individually variable or yoked neutral wedges in each parallel beam path to provide contrast change for each stimulus test pattern or both to provide constant mean luminance.

11. The apparatus of claim 2 wherein the ophthalmoscopy assembly further comprises an articulable eyepiece which may be adjusted so that the stimulus test target may be ophthalmoscopically placed in coarse steps at various retinal locations.

12. The apparatus of claim 11 wherein the eyepiece is functionally associated with an auxiliary telescope through which the retina may be directly observed to allow ophthalmoscopically placing the stimulus test target at a desired retinal location.

13. The apparatus of claim 2 wherein the spectral perimetry assembly comprises:
    (a) coordinate diaphragm placed adjacent the stimulus test pattern in each parallel beam path which may be adjusted to change the diameter of the projected stimulus test target.

14. The apparatus of claim 13 wherein the sensor comprises a radial potentiometer.

15. The eye examining apparatus of claim 13 wherein the spectral perimetry assembly further comprises a recording means for recording the stimulus test pattern locations and means for transmitting said locations from the sensors to the recording means.

16. The apparatus of claim 15 wherein the recording means comprises a polar coordinate plotter.

17. The apparatus of claim 15 wherein the recording means comprises a printer.

18. The apparatus of claim 1 wherein measurement assembly comprises:
    a) means for collecting and transmitting electroretinogram data from the eye;
    b) a differential preamplifier to accentuate electroretinogram waveform components;
    c) a filter element;
    d) means for determining a time-base average waveform;
    e) means for determining spectral sensitivity using electroretinogram component amplitudes as criteria; and
    f) a means for displaying the electroretinogram waveform data together with the perimetry data for where it was collected on the retina.

19. The apparatus of claim 18 wherein the means for displaying the electroretinogram waveform data comprises an oscilloscope.

20. The apparatus of claim 18 wherein the measurement assembly further comprises a means for storing signal traces.

21. A method for determining the electrical response of the retina of an eye to lights of different colors and spatial frequencies comprising the steps of:
    (a) ophthalmoscopically placing a stimulus onto a portion of the retina of an eye, whereby:
        (i) adjacent portions of the pattern alternate between white-spectral and spectral-white such that they appear to exchange places more than one time per second;
        (ii) the white portion of the stimulus pattern is fixed at a constant luminance and is used as a standard; and
        (iii) the spectral portion of the stimulus pattern is varied from dimmer than white to brighter than white;
    (b) determining the position of the stimulus on the retina; and
    (c) calculating the spectral sensitivity of the retina of the eye for a plurality of wavelengths.

22. The method of claim 21 wherein said white portion of the stimulus pattern is fixed at a constant luminance of 12000 Trolands.

23. The method of claim 21 wherein the adjacent portion of the pattern alternate between white-spectral and spectral-white such that they appear to change places 16 times per second.

* * * * *